US010684334B2

(12) United States Patent  
Uchida et al.

(10) Patent No.: US 10,684,334 B2  
(45) Date of Patent: Jun. 16, 2020

(54) MAGNETIC RESONANCE IMAGING APPARATUS AND PULSE DESIGN METHOD

(71) Applicant: Canon Medical Systems Corporation, Otawara-shi (JP)

(72) Inventors: Daisuke Uchida, Kawasaki (JP); Koji Akita, Yokohama (JP)

(73) Assignee: Canon Medical Systems Corporation, Otawara-shi (JP)

( * ) Notice: Subject to any disclaimer, the term of this patent is extended or adjusted under 35 U.S.C. 154(b) by 208 days.

(21) Appl. No.: 15/958,067

(22) Filed: Apr. 20, 2018

(65) Prior Publication Data  
US 2018/0313916 A1  Nov. 1, 2018

(30) Foreign Application Priority Data  
Apr. 28, 2017 (JP) ................................. 2017-090449

(51) Int. Cl.  
*G01R 33/36* (2006.01)  
*G01R 33/54* (2006.01)  
*G01R 33/58* (2006.01)  
*A61B 5/055* (2006.01)  
*G01R 33/483* (2006.01)  
(Continued)

(52) U.S. Cl.  
CPC .......... *G01R 33/3607* (2013.01); *A61B 5/055* (2013.01); *G01R 33/4833* (2013.01); *G01R 33/54* (2013.01); *G01R 33/543* (2013.01); *G01R 33/5659* (2013.01); *G01R 33/583* (2013.01); *G01R 33/246* (2013.01)

(58) Field of Classification Search  
CPC ............ G01R 33/3607; G01R 33/4833; G01R 33/543; G01R 33/5659; G01R 33/54; G01R 33/583; G01R 33/246; A61B 5/055  
See application file for complete search history.

(56) References Cited

U.S. PATENT DOCUMENTS 5,212,448 A * 5/1993 Le Roux ............. G01R 33/446  
324/307  
6,028,428 A * 2/2000 Cunningham ....... G01R 33/446  
324/307  
(Continued)

OTHER PUBLICATIONS

Suwit Saekho, et al., "Fast-$k_z$ Three-Dimensional Tailored Radiofrequency Pulse for Reduced $B_1$ Inhomogeneity", Magnetic Resonance in Medicine vol. 55, 2006, pp. 719-724.

*Primary Examiner* — Susan S Lee  
(74) *Attorney, Agent, or Firm* — Oblon, McClelland, Maier & Neustadt, L.L.P.

(57) ABSTRACT

According to one embodiment, a magnetic resonance imaging apparatus includes processing circuitry. The processing circuitry calculates inverse characteristics of a $B_1$ sensitivity map in an imaging area of a subject. The processing circuitry fits a multi-degree polynomial function to the inverse characteristics of the $B_1$ sensitivity map. The processing circuitry calculates positions in k-space, amplitudes and phases of a plurality of RF pulses by associating the polynomial function fit to the inverse characteristics with a relational expression between the RF pulses and k-space. The processing circuitry controls application of the RF pulses in accordance with the positions, the amplitudes and the phases. The polynomial function and the relational expression have equal degrees.

10 Claims, 8 Drawing Sheets

(51) Int. Cl.
*G01R 33/565* (2006.01)
*G01R 33/24* (2006.01)

(56) References Cited

U.S. PATENT DOCUMENTS 7,701,211 B2   4/2010   Katscher et al.
2012/0161766 A1   6/2012   Harvey et al.

\* cited by examiner

MAGNETIC RESONANCE IMAGING APPARATUS AND PULSE DESIGN METHOD

CROSS-REFERENCE TO RELATED APPLICATIONS

This application is based upon and claims the benefit of priority from the prior Japanese Patent Application No. 2017-090449, filed Apr. 28, 2017, the entire contents of all of which are incorporated herein by reference.

FIELD

Embodiments described herein relate generally to a magnetic resonance imaging apparatus and a pulse design method.

BACKGROUND

In magnetic resonance imaging apparatuses, it is important to realize magnetization distribution homogeneity to obtain MR images without an imbalance in sensitivity. However, there is a case where nonuniformity occurs in a spatial distribution of the high frequency magnetic field, i.e., a sensitivity map (hereinafter referred to as a "$B_1$ sensitivity map") of a radio frequency (RF) coil due to influence of a measurement target and a coil, which causes magnetic field inhomogeneity.

In order to mitigate inhomogeneity of the magnetic field, the amplitudes and the phases of the RF phases are properly controlled, and a strength distribution (hereinafter referred to as a "$B_1$ map design value") is applied onto the $B_1$ sensitivity map. If the RF pulses are properly controlled so that the $B_1$ map design values exhibit the inverse characteristics of the $B_1$ sensitivity map, the magnetization distribution obtained by the products of $B_1$ map design values and the $B_1$ sensitivity map becomes uniform.

The $B_1$ map design values are calculated by a method based on a linear approximation such as a small tip angle (STA) approximation, for example. The inhomogeneity of the high frequency magnetic field $B_1$ varies depending on a subject or a part of a subject to be measured. Accordingly, when planning design guidelines for RF pulses to be applied by using the STA approximation, an optimal design method is needed depending on the subject to be imaged.

DETAILED DESCRIPTION

In general, according to one embodiment, a magnetic resonance imaging apparatus includes processing circuitry. The processing circuitry is configured to calculate inverse characteristics of a $B_1$ sensitivity map in an imaging area of a subject. The processing circuitry is configured to fit a multi-degree polynomial function to the inverse characteristics of the $B_1$ sensitivity map. The processing circuitry is configured to calculate positions in k-space, amplitudes and phases of a plurality of RF pulses by associating the polynomial function fit to the inverse characteristics with a relational expression between the RF pulses and k-space. The processing circuitry is configured to control application of the RF pulses in accordance with the positions, the amplitudes and the phases. The polynomial function and the relational expression have equal degrees.

A magnetic resonance imaging apparatus and a pulse design method according to the present embodiment will be described with reference to the drawings. In the description below, structural elements having substantially the same functions and configurations will be denoted by the same reference symbols, and a repetitive description of such elements will be given only where necessary.

Figure 1:
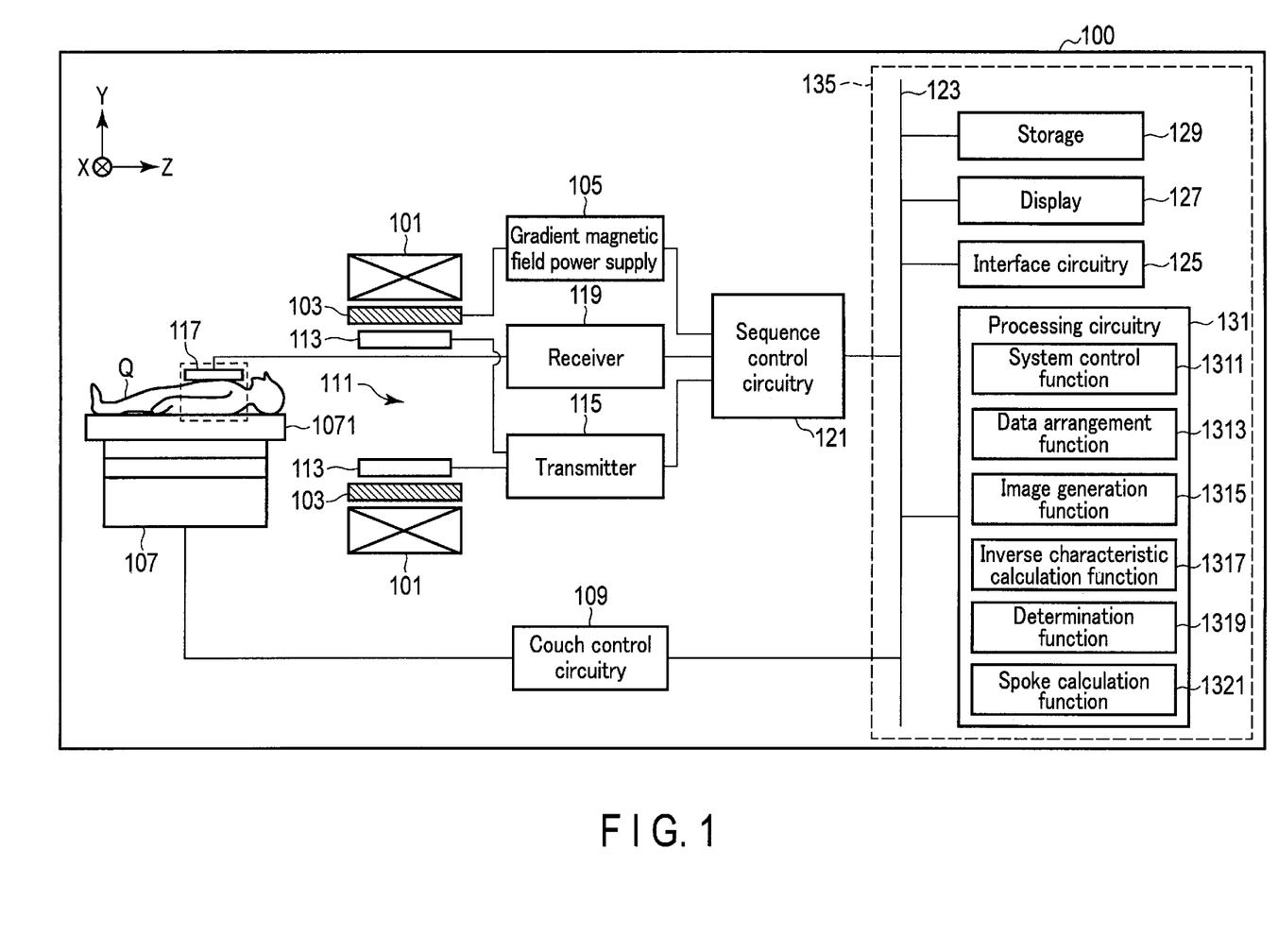
FIG. 1 is a block diagram of the configuration of a magnetic resonance imaging apparatus according to the present embodiment.

The configuration of a magnetic resonance imaging (MRI) apparatus according to the present embodiment will be described with reference to FIG. 1. FIG. 1 is a diagram showing the configuration of an MRI apparatus 100 according to the present embodiment.

As shown in FIG. 1, the MRI apparatus 100 includes a static field magnet 101, a gradient coil 103, a gradient magnetic field power supply 105, a couch 107, couch control circuitry 109, a transmitter coil 113, a transmitter (transmitting unit) 115, a receiver coil 117, a receiver (receiving unit) 119, sequence control circuitry (sequence controller) 121, a bus 123, interface circuitry (input unit) 125, a display 127, a storage 129, and processing circuitry (processor) 131. The MRI apparatus 100 may have a hollow cylindrical-shaped shim coil provided between the static field magnet 101 and the gradient coil 103.

The static field magnet 101 is a magnet formed in a hollow cylindrical shape, and generates a uniform static magnetic field ($B_0$) inside the hollow part. For example, a superconductive magnetic, etc. is used for the static field magnet 101. The non-illustrated shim coil may be formed in a hollow cylindrical shape inside the static field magnet 101. The shim coil is connected to a non-illustrated shim coil power supply, and homogenizes the static magnetic field generated by the static field magnet 101 by the power supplied from the shim coil power supply.

The gradient coil 103 is a hollow cylindrical-shaped coil, and is disposed inside the static field magnet 101. The gradient coil 103 is formed by combining three coils respectively corresponding to the X-, Y-, and Z-axes which are orthogonal to each other. The Z-axis direction is defined as the same as the direction of the static magnetic field. In addition, the Y-axis direction is a vertical direction, and the X-axis direction is a direction perpendicular to each of the Z-axis and the Y-axis. The three coils in the gradient coil 103 individually receive a current from the gradient magnetic field power supply 105 and respectively generate gradient magnetic fields in which magnetic field intensity changes along each of the X-, Y-, and Z-axes.

The gradient fields in the X-, Y-, and Z-axes generated by the gradient coil 103 respectively correspond to a frequency encode gradient field (readout gradient field), a phase encode gradient field, and a slice selective gradient field. The frequency encode gradient field is used to change the frequency of MR signals in accordance with a spatial position. The phase encode gradient field is used to change the phase of magnetic resonance (MR) signals in accordance with a spatial position. The slice selective gradient field is used to discretionarily determine an imaging slice.

The gradient magnetic field power supply 105 is a power supply apparatus that supplies a current to the gradient coil 103 by the control of the sequence control circuitry 121.

The couch 107 is an apparatus having the couch top 1071 on which a subject Q is placed. The couch 107 inserts the couch top 1071 on which the subject Q is placed into a bore 111 under the control of the couch control circuitry 109. Normally, the couch 107 is installed in an examination room where the MRI apparatus 100 is installed, in such a manner that the longitudinal axis of the couch 107 is parallel to the central axis of the static field magnet 101.

The couch control circuitry 109 is circuitry for controlling the couch 107, and is implemented by a processor, for example. The couch control circuitry 109 drives the couch 107 in accordance with an operator's instruction via the interface circuitry 125 to move the couch top 1071 in a longitudinal direction and a vertical direction.

The transmitter coil 113 is a radio frequency (RF) coil disposed inside the gradient coil 103. The transmitter coil 113 receives a high frequency pulse (RF pulse) from the transmitter 115, and generates transmission RF waves which correspond to a high frequency magnetic field. The transmitter coil is, for example, a whole body (WB) coil. The WB coil may be used as a transmitter/receiver coil. A cylindrical-shaped RF shield is provided between the WB coil and the gradient coil 103 to magnetically separate these coils.

The transmitter 115 supplies a high frequency pulse corresponding to a Larmor frequency to the transmitter coil 113 by the control of the sequence control circuitry 121. Specifically, the transmitter 115 includes an oscillation part, a phase selector, a frequency converter, an amplitude modulator, a high-frequency power amplifier, etc. The oscillation part generates a high-frequency signal of a resonance frequency specific to a target nucleus in the static magnetic field. The phase selector selects a phase of the high-frequency signal. The frequency converter converts a frequency of the high-frequency signal output from the phase selector. The amplitude modulator modulates an amplitude of the high-frequency signal output from the frequency converter, in accordance with a sin c function, for example. The high-frequency power amplifier amplifies the high-frequency signal output from the amplitude modulator. As a result of the operation of each element, the transmitter 115 outputs to the transmitter coil 113 a high frequency pulse corresponding to the Larmor frequency.

The receiver coil 117 is an RF coil disposed inside the gradient coil 103, and receives MR signals emitted from the subject Q by the high-frequency magnetic field. The receiver coil 117 outputs the received MR signals to the receiver 119. The receiver coil 117 is, for example, a coil array having one or more coil elements, typically having a plurality of coil elements. In FIG. 1, the transmitter coil 113 and the receiver coil 117 are illustrated as separate RF coils; however, the transmitter coil 113 and the receiver coil 117 may be implemented as an integrated transmitter/receiver coil. The transmitter/receiver coil is a local transmitter/receiver RF coil such as a head coil which corresponds to an imaging target of the subject Q, for example.

The receiver 119 generates magnetic resonance data (MR data) which is digitized complex data based on the MR signals output from the receiver coil 117 by the control of the sequence control circuitry 121. Specifically, the receiver 119 performs various signal processing such as pre-amplification, intermediate frequency conversion, phase detection, low-frequency amplification, filtering, etc. to the MR signals output from the receiver coil 117, and then performs analog-to-digital (A/D) conversion to the signals subjected to the signal processing. The receiver 119 executes sampling to the A/D converted data. By this processing, the receiver 119 generates MR data. The receiver 119 outputs the generated MR data to the sequence control circuitry 121. The MR data generated by the receiver 119 may be also referred to as raw data.

The sequence control circuitry 121 controls the gradient magnetic field power supply 105, the transmitter 115, and the receiver 119, in accordance with pulse sequence information output from the processing circuitry 131, and performs imaging on the subject Q. The pulse sequence information includes a magnitude of a current supplied from the gradient magnetic field power supply 105 to the gradient coil 103, timing of supplying a current by the gradient magnetic field power supply 105 to the gradient coil 103, a magnitude of an RF pulse supplied from the transmitter 115 to the transmitter coil 113, timing of supplying an RF pulse from the transmitter 115 to the transmitter coil 113, timing of receiving an MR signal from the receiver 119, etc. The magnitude of the current supplied from the gradient magnetic field power supply 105 to the gradient coil 103 corresponds to a waveform of the gradient field in accordance with the pulse sequence.

The bus 123 is a transmission path through which data is transmitted between the interface circuitry 125, the display 127, the storage 129, and the processing circuitry 131. The bus 123 may be connected to various biosignal measuring instruments, external storage devices, etc. through a network, etc.

The interface circuitry 125 is circuitry for receiving various instructions and information inputs from an operator. The interface circuitry 125 is circuitry for a pointing device, such as a mouse, or for an input device, such as a keyboard, etc. The interface circuitry 125 is not limited to circuitry for physical operation members such as a mouse, a keyboard, etc. For example, the interface circuitry 125 may include electric signal processing circuitry that receives an electric signal corresponding to an input operation through an external input device provided separately from the MRI apparatus 100 and outputs the received electric signal to various circuitry.

The display 127 displays various information, such as an MR image, etc. reconstructed by an image generation function 1315, under the control of a system control function 1311 in the processing circuitry 131. The display 127 is, for example, a CRT display, a liquid crystal display, an organic EL display, an LED display, a plasma display, any other display known in this technical field, or a monitor, etc.

The storage 129 stores MR data arranged in k-space by data arrangement function 1313, and image data generated by the image generation function 1315, etc. The storage 129 stores imaging conditions, etc. including various imaging protocols, and imaging parameters that define the imaging protocols. The storage 129 stores programs corresponding to the various functions executed by the processing circuitry 131. The storage 129 is, for example, a semiconductor memory element, such as a RAM (Random Access Memory) and a flash memory, a hard disk drive, a solid state drive, and an optical disk, etc. The storage 129 may be a drive, etc. configured to read and write various kinds of information with respect to a portable storage medium such as a CD-ROM drive, a DVD drive, or a flash memory, etc.

The processing circuitry 131 includes a non-illustrated processor, and a non-illustrated memory, such as a ROM or a RAM, etc. as hardware resources, to integrally control the MRI apparatus 100. The processing circuitry 131 includes the system control function 1311, the data arrangement function 1313, the image generation function 1315, an inverse characteristic calculation function 1317, a determination function 1319, and a spoke calculation function 1321. The system control function 1311, the data arrangement function 1313, the image generation function 1315, the inverse characteristic calculation function 1317, the determination function 1319, and the spoke calculation function 1321 are stored in the storage 129 each in a form of a computer-executable program. The processing circuitry 131 is a processor which reads a program corresponding to each function from the storage 129 and executes the program to realize the corresponding function. In other words, the processing circuitry 131 which has read each program has the corresponding function in the processing circuitry 131 of FIG. 1.

FIG. 1 illustrates that the aforementioned functions are realized by single processing circuitry 131; however, the processing circuitry 131 may include a plurality of independent processors, and the functions may be realized by the processors executing respective programs. In other words, there may be a case where each of the aforementioned functions may be configured as a program, and single processing circuitry executes each program, or a case where each of the functions may be implemented in independent program-execution circuitry specific to respective functions. The system control function 1311, the data arrangement function 1313, the image generation function 1315, the inverse characteristic calculation function 1317, the determination function 1319, and the spoke calculation function 1321 included in the processing circuitry 131 are an example of a controller, a data arrangement unit, an image generation unit, a first calculation unit, a fitting unit, and a second calculation unit, respectively.

The term "processor" used in the above description means, for example, a CPU (Central Processing Unit), a GPU (Graphics Processing Unit), or circuitry such as an ASIC (Application Specific Integrated Circuit), a programmable logic device (for example, an SPLD (Simple Programmable Logic Device), a CPLD (Complex Programmable Logic Device), or an FPGA (Field Programmable Gate Array)).

The processor reads and executes a program stored in the storage 129 to realize the corresponding function. A program may be directly integrated into the circuitry of the processor, instead of storing the program on the storage 129. In this case, the processor reads and executes a program integrated into the circuitry to realize the corresponding function. Similarly, the couch control circuitry 109, the transmitter 115, the receiver 119, and the sequence control circuitry 121, etc. are also configured as electronic circuitry, such as the above processor, etc.

The processing circuitry 131 integrally controls the MRI apparatus 100 by the system control function 1311. Specifically, the processing circuitry 131 reads a system control program stored in the storage 129, deploys the program on a memory, and controls the respective circuitry of the MRI apparatus 100 in accordance with the deployed system control program.

Figure 2:
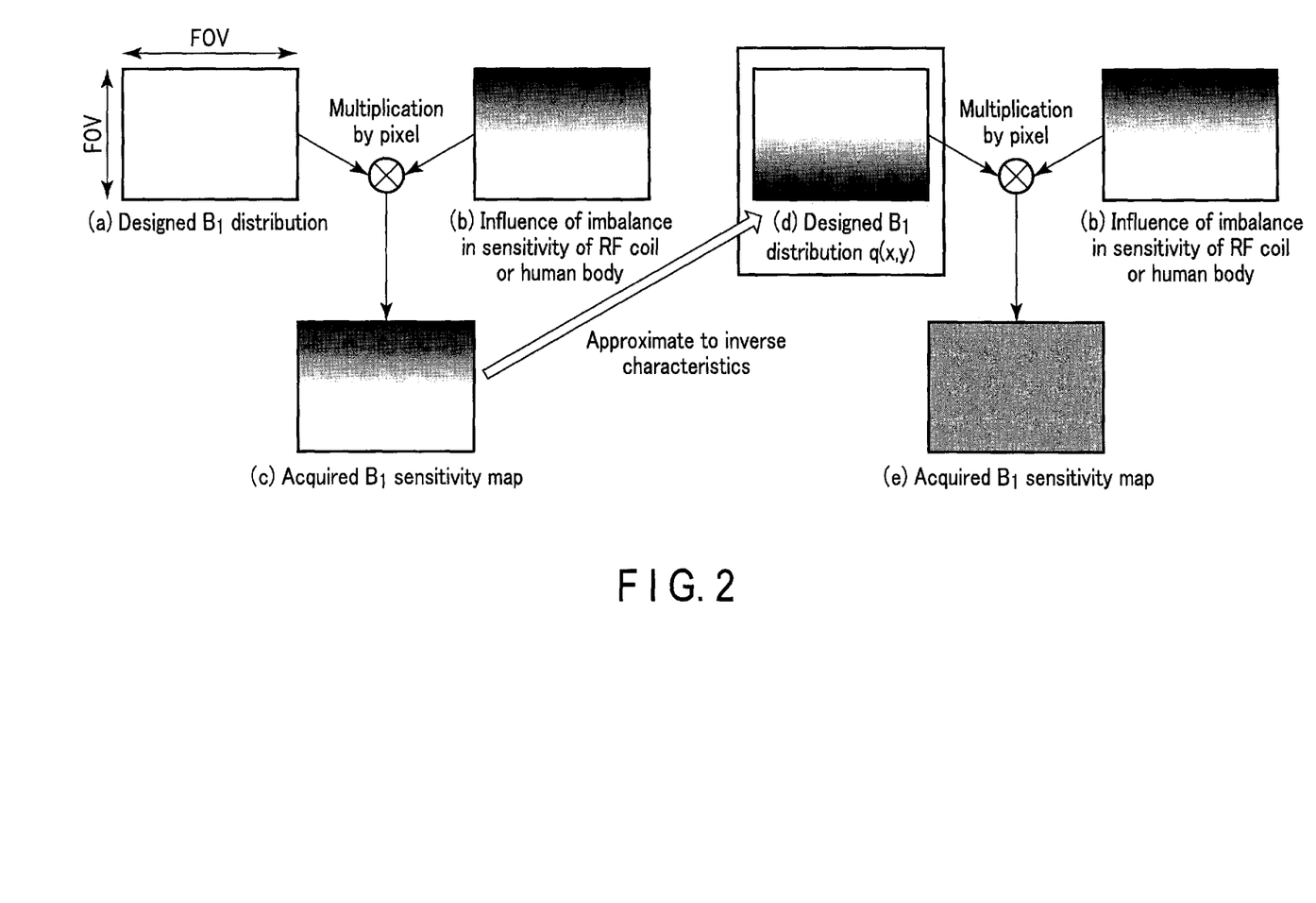
FIG. 2 is a diagram illustrating a method for mitigating inhomogeneity in the $B_1$ sensitivity map assumed in the present embodiment.

A method for mitigating the $B_1$ sensitivity map inhomogeneity assumed in the present embodiment is described with reference to the diagram of FIG. 2.

In general, the $B_1$ distribution is designed so that the $B_1$ distribution is uniform in an imaging area, as in "(a) designed $B_1$ distribution". However, in the actual cases, the magnetic field is affected by an imbalance in sensitivity of the RF coil or a human body, as indicated as gradation in "(b) influence of imbalance in sensitivity of RF coil or human body". The $B_1$ sensitivity map actually acquired by the RF coil that indicates the spatial sensitivity of the receiver coil is as shown as "(c) acquired $B_1$ sensitivity map" in FIG. 2 in which "(b) influence of an imbalance in sensitivity of RF coil or human body" is exerted on each pixel of the (a) designed $B_1$ distribution, and the (c) acquired $B_1$ sensitivity map exhibits sensitivity inhomogeneity.

If a strength distribution is superimposed onto the $B_1$ distribution to generate "(d) designed $B_1$ distribution" which has the inverse characteristics of "(c) acquired $B_1$ sensitivity map" which shows inhomogeneity, the influence on the magnetic field indicated in (b) can be mitigated by exerting the influence (b) on the "(d) designed $B_1$ distribution". As a result, the MRI apparatus can acquire "(e) acquired $B_1$ sensitivity map" which shows homogeneity.

The inverse characteristics of the "(c) acquired $B_1$ sensitivity map" can be theoretically calculated; however, it is difficult to realize the "(d) designed $B_1$ distribution" which has the inverse characteristics of the "(c) acquired $B_1$ sensitivity map" by the RF pulses actually generated by the transmitter coil.

The MRI apparatus according to the present embodiment associates a polynomial function expressing the inverse characteristics of the $B_1$ sensitivity map with a relational expression between RF pulses and k-space (a spoke relational expression in this embodiment), and calculates parameters of RF pulses (position in k-space, and amplitude and phase of the RF pulse) to be used in the spoke technique. Namely, applying RF pulses based on the calculated position in k-space, amplitude, and phase, the designed $B_1$ distribution which approximates with high accuracy to the inverse characteristics of the $B_1$ sensitivity map can be generated by actually applied RF pulses. Accordingly, the MRI apparatus can acquire a homogeneous $B_1$ sensitivity map in which influences to the magnetic field are eliminated.

Figure 3:
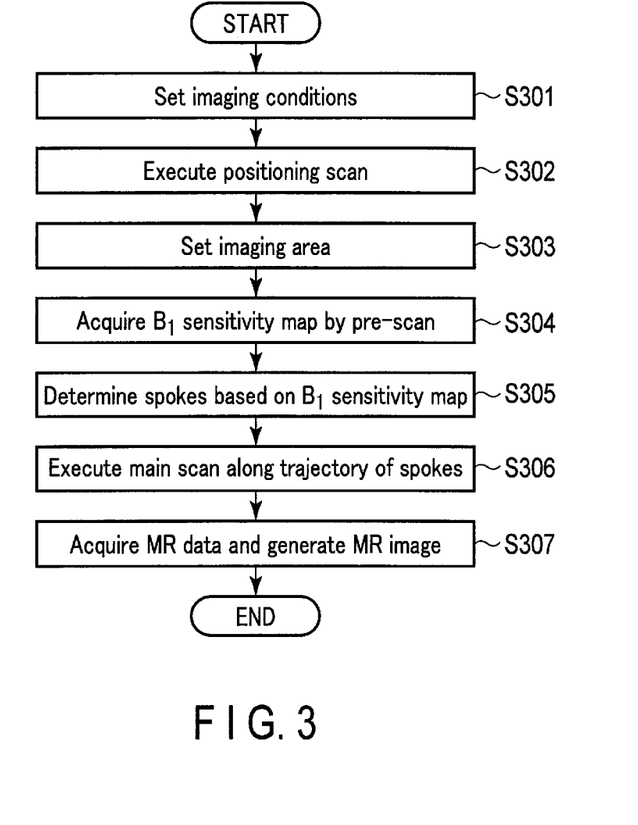
FIG. 3 is a flowchart of the imaging processing of the magnetic resonance imaging apparatus according to the present embodiment.

The imaging processing by the MRI apparatus according to the present embodiment will be explained with reference to the flowchart of FIG. 3.

In step S301, imaging conditions are set. For example, the processing circuitry 131 may set the imaging conditions by reading imaging conditions stored in the storage 129, in response to an operator's instruction input through the interface circuitry 125. The imaging condition may include, for example, an imaging target of a subject, an imaging time, and contrast, etc.

In step S302, a positioning scan is performed. The positioning scan is executed in accordance with an imaging protocol to generate a positioning image used in positioning for a main scan. Specifically, the sequence control circuitry 121 executes the positioning scan to an imaging target, in accordance with the imaging protocol for positioning scan. By the image generation function 1315, the processing circuitry 131 generates a positioning image based on MR data obtained by the positioning scan.

In step S303, an imaging area is set on the positioning image generated by the positioning scan. Specifically, an imaging position for the main scan is input by an operator through the interface circuitry 125, for example. The imaging area is determined by the input of the imaging position.

In step S304, pre-scan is performed relative to the imaging area to obtain a $B_1$ sensitivity map, and the $B_1$ sensitivity map is acquired. Specifically, the sequence control circuitry 121 controls the gradient magnetic field power supply 105 and each circuitry in accordance with the imaging area and the pulse sequence for pre-scan to obtain a $B_1$ sensitivity map, and performs imaging on the subject.

The processing circuitry 131 generates, by the image generation function 1315, a $B_1$ sensitivity map in the imaging area based on the acquired MR data. The $B_1$ sensitivity map is represented as a two-dimensional coordinate space (x-y plane) in which each pixel has a pixel value.

In the case where it is assumed that a change in the $B_1$ sensitivity map is less, for example in the case where a single subject is imaged successively, the $B_1$ sensitivity map acquired in the previous imaging is used, and step S304 may be skipped.

In step S305, the processing circuitry 131 determines, by the spoke calculation function 1321, spokes based on the $B_1$ sensitivity map, and calculates positions in k-space, amplitudes, and phases of the RF pulses corresponding to the spokes.

In step S306, transmission pulses to be applied in the order according to the trajectory of spokes are generated based on the calculated positions in k-space, amplitudes, and phases of the RF pulses, and data acquisition is executed in accordance with a data acquisition sequence, i.e., the main scan, by using the transmission pulses. Specifically, the processing circuitry 131 controls, by the system control function 1311, the sequence control circuitry 121 so that RF pulses are applied along the trajectory of spokes (described later), in accordance with the imaging area and the imaging protocol for the main scan using spokes, and executes the main scan. The method for determining spokes and the method for application of RF pulses based on spokes will be described later in detail.

In step S307, MR signals generated in the data acquisition sequence, which is the main scan, are acquired as MR data, and an MR image is generated. Specifically, the processing circuitry 131 generates, by the image generation function 1315, an MR image based on acquired MR data. The imaging processing is completed by the above steps.

The data acquisition sequence, which is the main scan, indicates various imaging pulse sequences used in MRI, such as the FE (Field Echo) method (or the GRE (Gradient Echo) method), the SE (Spin Echo) method, and the FSE (Fast Spin Echo) method. The transmission pulses designed by the spoke technique are used at least as part of the transmission pulses in the data acquisition sequence, and an image is generated by the acquired data.

Figure 4:
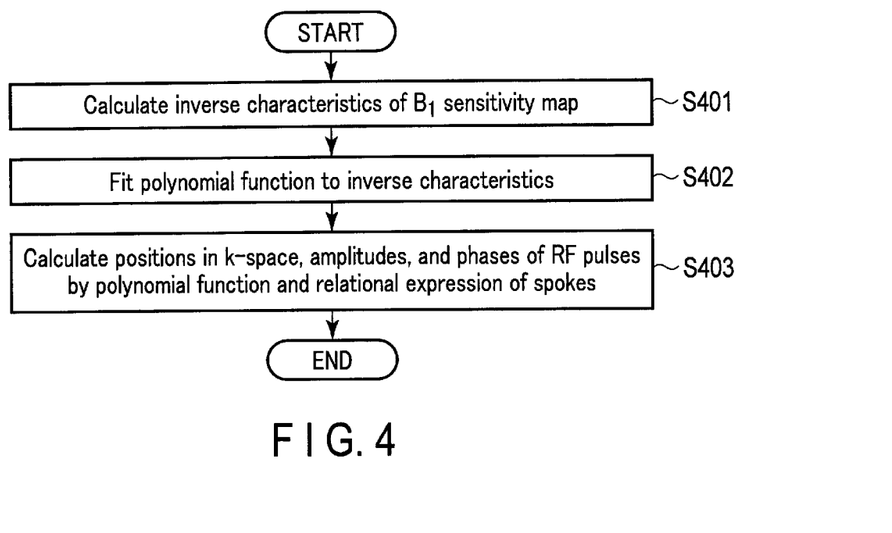
FIG. 4 is a flowchart of the determination processing of spokes in step S305.

The processing of determining spokes as shown in step S305 of FIG. 3 will be explained with reference to the flowchart of FIG. 4.

In step S401, the processing circuitry 131 acquires, by the inverse characteristic calculation function 1317, inverse characteristics of the $B_1$ sensitivity map within the imaging area of the subject Q. The inverse characteristics of the $B_1$ sensitivity map may be acquired, for example, by calculating a reciprocal of each coordinate value (pixel value) of the $B_1$ sensitivity map, or by using the general technique.

In step S402, the processing circuitry 131 performs, by the determination function 1319, fitting relative to the inverse characteristics of the $B_1$ sensitivity map. Here, a polynomial function of degree 2 is used for the fitting. The "fitting" indicates determining factors and a constant of a polynomial function P which is represented by equation (1), for example. That is, the inverse characteristics of the $B_1$ sensitivity map are substituted for the polynomial function P, and are represented by the polynomial function P.

$$P = ax^2 + by^2 + cx + dy + exy + f \qquad (1)$$

In equation (1), x and y respectively represent pixel positions in the X direction and the Y direction in the X-Y plane of the $B_1$ sensitivity map. The values of each factor (a, b, c, d, and e) and constant f may be obtained by substituting coordinate values in the inverse characteristics of the $B_1$ sensitivity map for equation (1). For example, if the $B_1$ sensitivity map is represented by n×n pixels, the factors and the constant may be determined by the matrix multiplication of equation (2).

$$\begin{bmatrix} a \\ b \\ c \\ d \\ e \\ f \end{bmatrix} = \begin{bmatrix} x_1^2 & y_1^2 & x_1 & y_1 & x_1 y_1 & 1 \\ x_2^2 & y_2^2 & x_2 & y_2 & x_2 y_2 & 1 \\ & & \vdots & & & \\ x_n^2 & y_n^2 & x_n & y_n & x_n y_n & 1 \end{bmatrix}^{-1} \begin{bmatrix} p_1 \\ p_2 \\ \vdots \\ p_n \end{bmatrix} \qquad (2)$$

In equation (2), $p_i$ (i=1, . . . , n) is a pixel value of each coordinate ($x_i$, $y_i$) of the inverse characteristics of the $B_1$ sensitivity map.

In step S403, the processing circuitry 131 associates, by the spoke calculation function 1321, the polynomial function P in which the factors are determined by the fitting in step S402 with the spoke relational expression (quadratic equation in this embodiment), and analytically solves the spoke relational expression using the polynomial function P.

Figure 5:
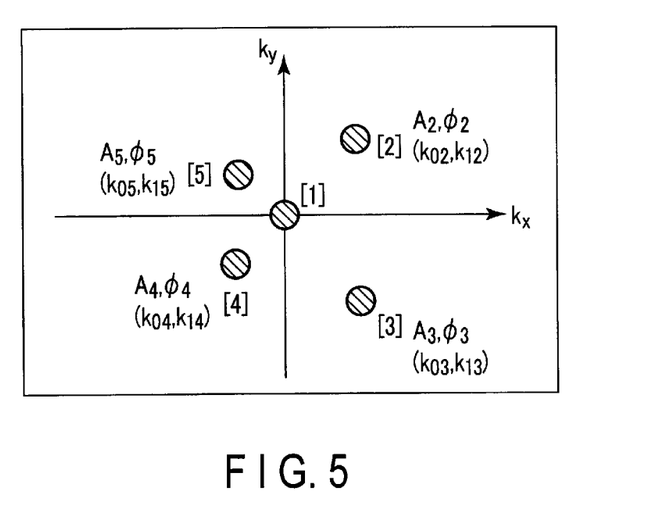
FIG. 5 illustrates an example of spoke positions in k-space.

Spokes can be expressed by superposing the cosine functions. In accordance with FIG. 5 which indicates the spoke positions in k-space, the spokes can be represented by the quadratic equation as shown in equation (3).

$$q(x, y) = A_1 + 2A_4 \{\cos(2\pi k_{04} x + 2\pi k_{14} y + \phi_4)\} + \qquad (3)$$
$$2A_5 \{\cos(2\pi k_{05} + 2\pi k_{15} y + \phi_5)\} \approx$$
$$-4\pi^2 (k_{04}^2 A_4 + k_{05}^2 A_5) x^2 - 4\pi^2 (k_{14}^2 A_5 + k_{15}^2 A_5) y^2 -$$
$$4\pi (k_{04} \phi_4 A_4 + k_{05} \phi_5 A_5) x - 4\pi (k_{14} \phi_4 A_4 + k_{15} \phi_5 A_5) y -$$
$$8\pi^2 (k_{04} k_{14} A_4 + k_{05} k_{15} A_5) xy + (A_1 2 A_4 + 2 A_5 - A_4 \phi_4^2 - A_5 \phi_5^2)$$

Accordingly, by the processing in which the processing circuitry 131 associates, by the spoke calculation function 1321, the polynomial function P with the spoke relational expression, and analytically solves the spoke relational expression, positions in k-space ($k_x$, $k_y$), amplitudes, and phases ($A_n$, $\varphi_n$) that are parameters relating to RF pulses are uniquely determined.

The processing circuitry 131 is not limited to analytically solve the polynomial function P and the spoke relational expression, it may also approximately solve them.

Next, an example method of applying RF pulses using the spoke technique will be explained with reference to FIGS. 6 and 7.

The spoke technique is to mitigate inhomogeneity of the $B_1$ distribution by the $B_1$ distribution that can be generated by slice-selective pulses dispersed in k-space. If a flip angle is small, the transverse magnetization can be linearly approximated using the magnitude of magnetization vector $M_0$ by STA (Small Tip Angle) approximation. By this process, the Bloch equation can be simplified, and accordingly, the k-space and the real space can be assumed as a Fourier transform pair.

Figure 6:
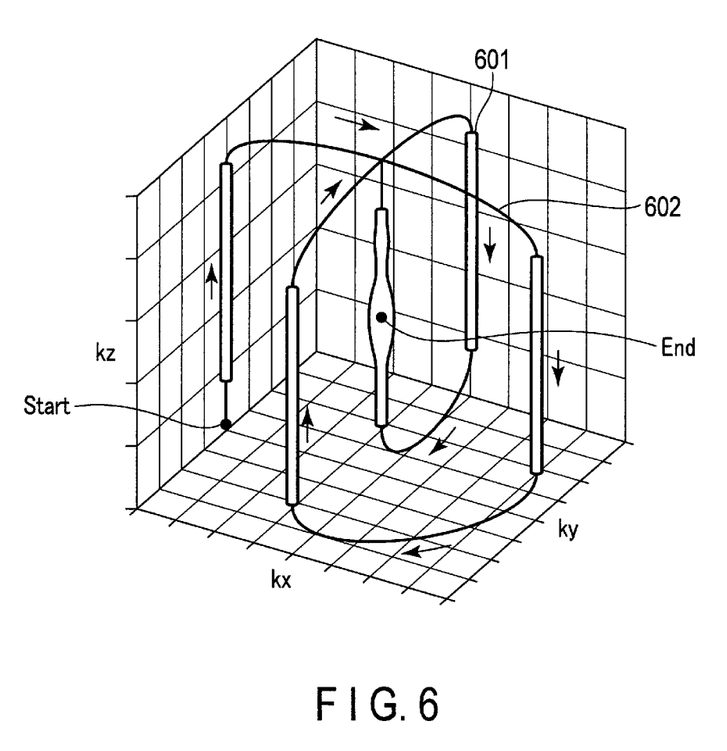
FIG. 6 illustrates a trajectory of spokes in k-space.

FIG. 6 illustrates a trajectory of spokes in k-space. In the spoke technique, lines (dots in $k_x$-$k_y$ plane) of impulse (delta function) parallel to the $k_z$ axis shown in k-space are also referred to as spokes. In an example shown in FIG. 6, five spokes 601 are provided, and each spoke 601 is connected (selected) along a trajectory 602 from a "start" position to an "end" position. The trajectory 602 is a trajectory that indicates the positions of the spokes 601 in k-space expressed by $k_x$-axis, $k_y$-axis, and $k_z$-axis, and indicates an order of applying RF pulses corresponding to the spokes 601.

Each of the spokes 601 is associated with parameters (an amplitude and a phase) of an RF pulse corresponding to a position of corresponding spokes 601 in k-space. An RF pulse having an amplitude and a phase corresponding to each spoke 601 is applied as a sub-pulse. That is, RF pulses are designed to be an excitation pulse as an entirety of a plurality of sub-pulses. The spoke technique is also referred simply to as "spoke".

In an example shown in FIG. 6, five spokes are used. However, the number of spokes is not limited thereto, and it may be the case where three or more spokes 601 including a spoke at the k-space origin used for offset are adopted.

As the number of the spokes 601 increases, the number of sub-pulses to be applied increases, thereby increasing a time required to form an excitation pulse. Accordingly, the RF pulses may be designed to adopt an appropriate number of spokes 601 in consideration of the imaging time.

An example of transmission pulses along the trajectory 602 of the spokes 601 as shown in FIG. 6 will be explained with reference to FIG. 7.

Figure 7:
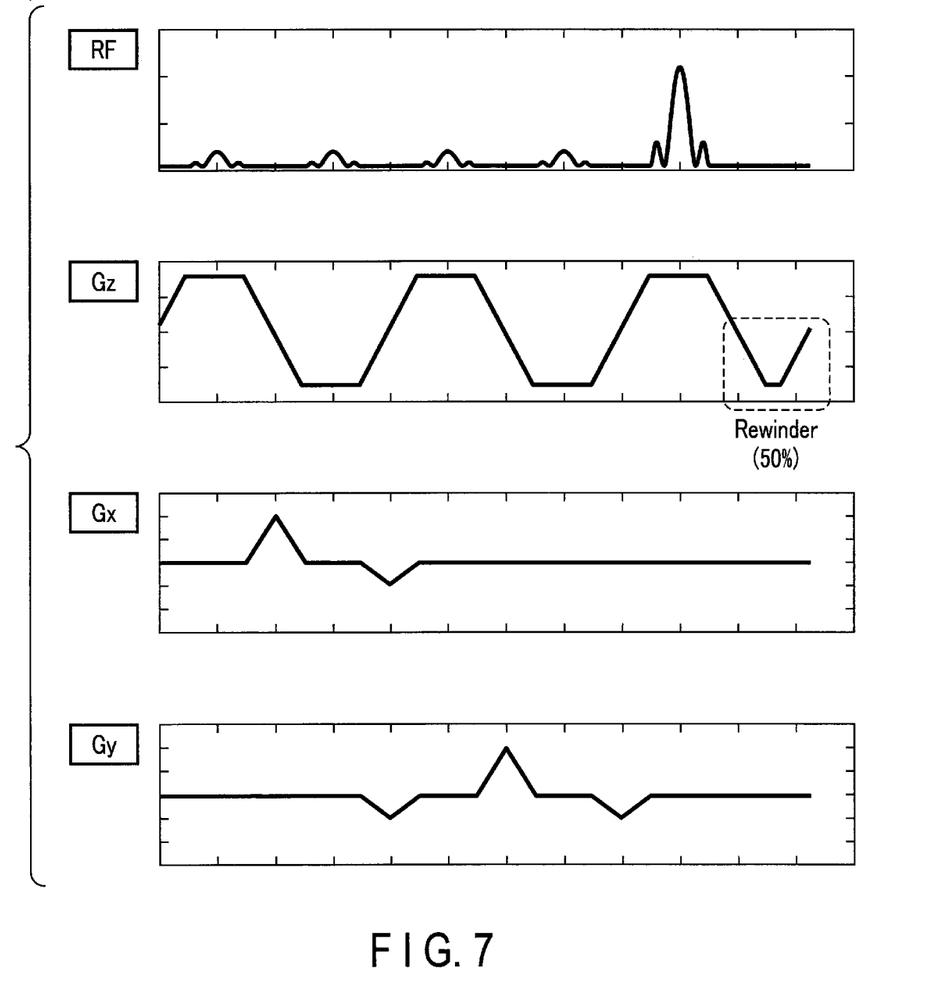
FIG. 7 illustrates an example of a transmission pulse according to the trajectory shown in FIG. 6.

FIG. 7 shows the graphs of the amplitude of RF pulses, the gradient field Gz in z-direction, the gradient field Gx in x-direction, and the gradient field Gy in y-direction, from the top to bottom. In the graphs, the vertical axis represents strength, and the horizontal axis represents time. The gradient fields Gz, Gx, and Gy respectively correspond to the slice selective gradient field, the frequency encode gradient field, and the phase encode gradient field. The slice selective gradient field is used to discretionarily determine an imaging slice. The phase encode gradient field is used to change the phase of MR signals in accordance with spatial positions. The frequency encode gradient field is used to change the frequency of MR signals in accordance with spatial positions.

RF pulses each corresponding to the respective spokes may be applied as sub-pulses along the trajectory 602 of the spokes 601 while applying the gradient fields Gx, Gy, and Gz. In the following description, the sequence control circuitry 121 may control RF pulse application based on the control of the system control function 1311, for example.

The RF pulse application based on the pulse sequence using spokes will be explained with reference to FIGS. 6 and 7 in detail. First, an RF pulse with a phase and an amplitude corresponding to the first spoke from the position of "start" is applied as a first sub-pulse, while the gradient field Gz is applied.

After the first sub-pulse is applied, the gradient field Gx of a positive value is applied. Thereafter, an RF pulse with a phase and an amplitude corresponding to the second spoke is applied as a second sub-pulse, while the gradient field Gz having a negative value is applied. In this process, the MRI apparatus according to the present embodiment can apply RF pulses along the trajectory 602 of the spokes 601 as shown in FIG. 6.

Similarly, the gradient fields Gx and Gy are applied to determine the trajectory in k-space, and RF pulses corresponding to the third and fourth spokes are applied while the gradient field Gz is applied. Finally, an RF pulse corresponding to the fifth spoke may be applied after bringing the trajectory back to the origin of a $k_x$-$k_y$ plane in k-space.

In FIG. 7, a rewinder is applied to the gradient field Gz to bring the trajectory back to the origin in three-dimensional k-space. However, this process is not essential. The rewinder of the gradient field Gz has approximately 50% of an area of a pulse in Gz. Although it is not illustrated in Gx or Gy, a rewinder may be applied to Gx or Gy at the same timing as application of the rewinder in Gz, to bring the total area of applied pulse to be zero.

In the case where the coordinates of an imaging area in the real space are expressed by a pixel, the unit of coordinates in k-space is "1/pixel". For example, by the system control function 1311 or the spoke calculation function 1321, the processing circuitry 131 may convert the coordinate unit in k-space to be "1/cm=$cm^{-1}$" by using the conversion formula between pixels and centimeters.

For example, a size of 128×128 pixels in the real space is converted so that a pixel is "1/128" in k-space. In the case where a size of 128×128 pixels is 10×10 cm in the real space, a pixel can be converted into $10/128$ cm in the real space by calculating the ratio of "cm/pixel", and accordingly, a unit in k-space is converted into "1/cm", namely, "(128/10) $cm^{-1}$". This conversion has an advantage that the converted values can be used as-is when the gradient fields Gx, Gy and Gz are applied.

In addition, the amplitude to be calculated is an index indicating the relative amount of amplitude of each sub-pulse, which is a dimensionless value. Accordingly, when calculating a flip angle of each sub-pulse, the processing circuitry 131 may calculate, by the system control function 1311, a desired flip angle×((RF sub-pulse amplitude)/(sum of RF sub-pulse amplitudes)). For example, it is assumed that a flip angle is set to be 90 degree by applying the first RF pulse to the fifth RF pulse respectively corresponding to the five spokes. To obtain a flip angle of the first RF pulse, the processing circuitry 131 may calculate, by the system control function 1311, 90 degree×(A1/(A1+A2+A3+A4+A5)), where the amplitudes of the first RF pulse to the fifth RF pulse are represented as A1 to A5.

The polynomial function used for fitting may be changed depending on the state of the $B_1$ sensitivity map obtained in the imaging area. An example of using different polynomial functions will be explained with reference to FIGS. 8A and 8B.

Figure 8A:
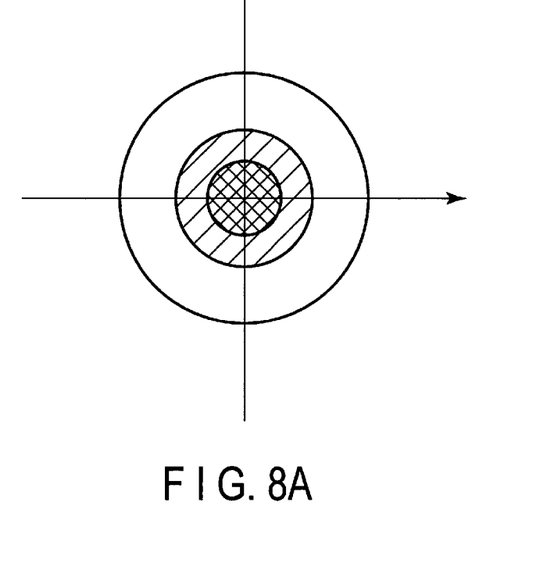
FIG. 8A illustrates an example of a $B_1$ sensitivity map of a head.

FIG. 8A illustrates an example of a $B_1$ sensitivity map of a head. In the x-y plane of the $B_1$ sensitivity map, the $B_1$ strength is high in the central part, and decreases concentrically from the central part toward the outer peripheral. This strength distribution shows a symmetric distribution with the origin as a center.

For the $B_1$ sensitivity map having this kind of symmetric distribution, the $B_1$ sensitivity map inhomogeneity can be mitigated by spokes positioned on the $k_x$-axis and $k_y$-axis in k-space. Thus, in this case, the polynomial function having $x^2$, $y^2$, x, y, and a constant as terms ($P=ax^2+by^2+cx+dy+e$) may be used for fitting.

Figure 8B:
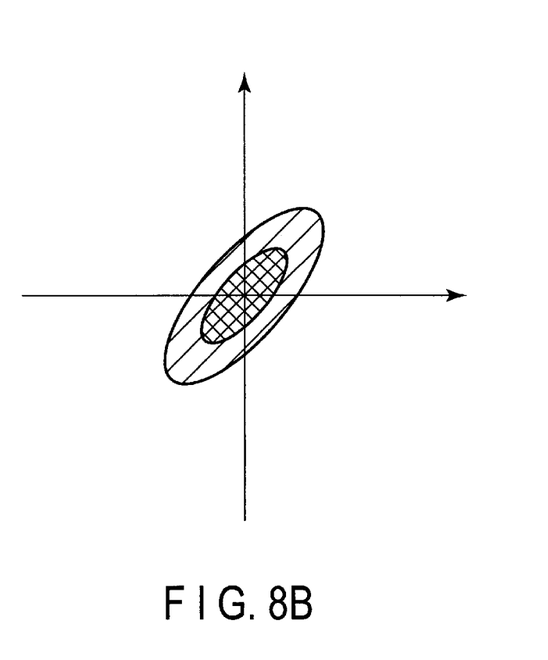
FIG. 8B illustrates an example of a $B_1$ sensitivity map of an abdomen.

FIG. 8B illustrates an example of a $B_1$ sensitivity map of an abdomen. For the $B_1$ sensitivity map having an asymmetric distribution in view of the origin, complex correction is necessary, and spokes are needed to be placed deviated from the $k_x$-axis and $k_y$-axis in k-space. Accordingly, the polynomial function of equation (1) having "xy" as a term may be used for fitting.

That is, the polynomial function used for fitting is changed depending on whether the $B_1$ sensitivity map of the imaging area is symmetric or asymmetric. If the map shows symmetric distribution, the number of terms can be reduced, and accordingly, the polynomial function and the spoke relational expression can be simply associated with each other. Therefore, analysis for determining positions in k-space, amplitudes, and phases can be simplified.

The detailed processing will be described. For example, an algorithm relating to the aforementioned two kinds of polynomial functions is stored in the storage 129, etc. The processing circuitry 131 determines, by the system control function 1311, whether the $B_1$ sensitivity map of the imaging area is symmetric or asymmetric. If the $B_1$ sensitivity map is symmetric, the processing circuitry 131 uses, by the determination function 1319, the polynomial function ($P=ax^2+by^2+cx+dy+e$) to perform fitting relative to the inverse characteristics of the $B_1$ sensitivity map. On the other hand, if the $B_1$ sensitivity map is asymmetric, the processing circuitry 131 uses, by the determination function 1319, the polynomial function ($P=ax^2+by^2+cx+dy+exy+f$) to perform fitting relative to the inverse characteristics of the $B_1$ sensitivity map.

The processing circuitry 131 chooses, by the spoke calculation function 1321, the spoke relational expression to be associated with the polynomial function, depending on the number of degrees or the number of terms of the polynomial function to be used.

If fitting is performed with the polynomial function ($P=ax^2+by^2+cx+dy+e$) that is used for the symmetric $B_1$ sensitivity map, the processing circuitry 131 may determine, by the system control function 1311, whether the polynomial function that is a quadratic function opens upward or downward. If the quadratic function opens upward, the processing circuitry 131 uses, by the spoke calculation function 1321, the spoke relational expression in which phase is shifted by π (pi). In this case, the polynomial function used for the fitting can be optimally associated with the spoke relational expression in analysis.

In the case where the polynomial function P and the spoke relational expression are analytically solved by using the polynomial function P of equation (1), there may be a case where a non-realistic value is obtained as a solution, such as a negative amplitude value. Accordingly, to obtain a realistic value as a solution, the processing circuitry 131 may set, by the spoke calculation function 1321, a conditional equation of k-space coordinates so that the amplitude of spokes passing through the origin does not become a negative value.

In addition, in the case where the polynomial function P of equation (1) is used, a discriminant may be used to utilize the characteristics of quadric curve (hyperbola, ellipse, parabola, etc.). For example, the processing circuitry 131 may set, by the spoke calculation function 1321, positions in k-space and phases of RF pulses, based on the focus point or the axis of the quadric curve used as a reference.

Furthermore, in the case where the polynomial function P of equation (1) is used, the processing circuitry 131 may change, by the spoke calculation function 1321, an approximation method used in the spoke relational expression when analytically solving the relational expression, if the phrase in the spoke relational expression is deviated from zero degrees by a threshold value or more.

For example, if θ is a deviation less than a threshold value from zero degrees, for example, θ is to be approximated to zero degrees, θ may be approximated as "cos θ=1−θ²/2". If θ is a deviation equal to or more than the threshold value from zero degrees, for example, θ is to be approximated to π, θ may be approximated as "cos θ=−1+(θ−π)²/2".

An example of a $B_1$ sensitivity map before and after application of spokes will be explained with reference to FIGS. 9A and 9B.

Figure 9A:
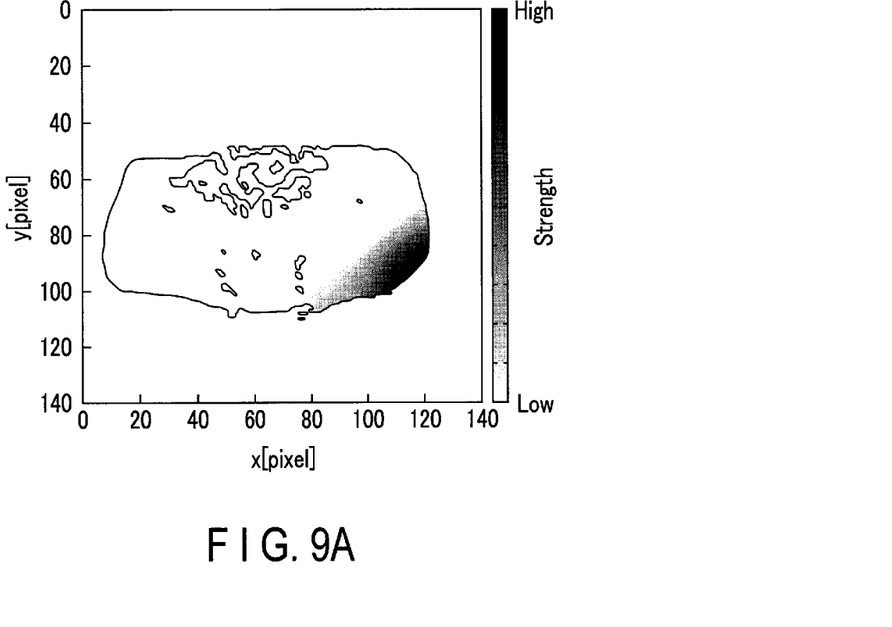
FIG. 9A illustrates an example of a $B_1$ sensitivity map of an abdomen before spoke application.

FIG. 9A illustrates an example of a $B_1$ sensitivity map of an abdomen before spoke application. FIG. 9B illustrates an example of a $B_1$ sensitivity map of an abdomen after spoke application. In FIGS. 9A and 9B, the vertical axis represents pixel values in the y-direction, and the horizontal axis represents pixel values in the x-direction. The strength distribution of magnetic field is expressed as a gradation.

As shown in FIG. 9A, the $B_1$ sensitivity map before spoke application shows imbalance in the strength of the magnetic field, and the magnetic field distribution is inhomogeneous.

Figure 9B:
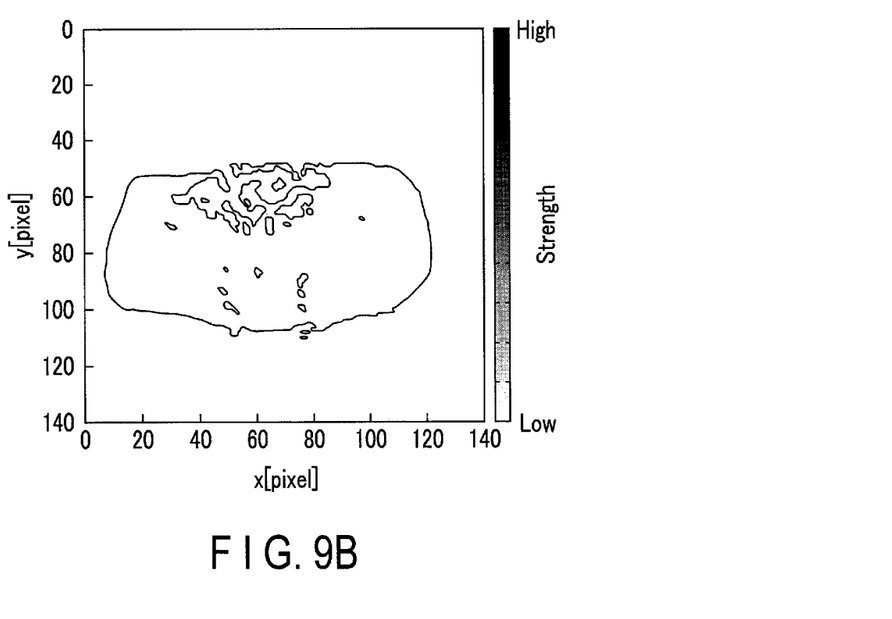
FIG. 9B illustrates an example of a $B_1$ sensitivity map of an abdomen after spoke application.

On the other hand, as shown in FIG. 9B, the $B_1$ sensitivity map after spoke application shows homogeneity in the strength of the magnetic field, and the magnetic field homogeneity is accomplished.

According to the aforementioned embodiment, the polynomial function is fit to the inverse characteristics of the $B_1$ sensitivity map, and the polynomial function and the spoke relational expression are associated with each other and analytically solved. By this process, positions in k-space, amplitude and phases of RF pulses used for the spoke technique can be uniquely calculated. Accordingly, by using the RF pulses based on the calculated positions in k-space, amplitude, and phases, the $B_1$ distribution generated by the RF pulses can be approximated to the inverse characteristics of the $B_1$ sensitivity map with high precision. As a result, the $B_1$ sensitivity map inhomogeneity can be mitigated simply and with high precision.

In the present embodiment, spokes are determined in accordance with the inverse characteristics of the acquired $B_1$ sensitivity map. However, spokes to be applied may be predetermined in accordance with the imaging conditions such as age, gender, and weight, and an imaging target, etc. of a subject.

For example, the correspondence information between the imaging conditions and the spoke relational expression to be applied is prepared as a table, and the table is stored in the storage 129, etc. If the imaging area is set, the processing circuitry 131 determines, by the spoke calculation function 1321, the spoke relational expression to be applied by referring to the table, based on the imaging conditions of the subject. RF pulses are applied along the trajectory of the determined spokes, and the main scan is performed.

This processing can eliminate the need of determining spokes every time imaging is performed, and accordingly, the time required for spoke generation can be reduced.

The polynomial function and the spoke relational expression used for the aforementioned fitting are associated by quadratic functions. However, a function of a higher degree may be used as long as the degree is the same as the polynomial function and the spoke relational expression. For example, the spoke relational expression can be expressed by a function of a higher degree by Taylor series expansions of a cosine function, i.e., a function of (2n−1) degrees. If a polynomial function of a higher degree than a quadratic function is adopted for the polynomial function and the spoke relational expression used for fitting, reproducibility of the $B_1$ sensitivity map by a fitting function can be further improved with the processing similar to the case where the quadratic function is adopted. As a result, the $B_1$ sensitivity map inhomogeneity can be mitigated with higher precision, which also mitigates inhomogeneity in the magnetic field.

The functions of the processing circuitry 131 explained in the embodiment can be executed based on a software program. The functions of the processing circuitry 131 are stored in a magnetic disc (flexible disc, hard disc, etc.), an optical disc (CD-ROM, CD-R, CD-RW, DVD-ROM, DVD±R, DVD±RW, etc.), a semiconductor memory, or a similar storage medium, as a program executable by a computer. As long as a storage medium is readable by a computer or a built-in system, any storage format can be adopted. In this case, the functions of the processing circuitry 131 can be realized by a computer reading the program from the storage medium and executing instructions written in the program on the CPU. In addition, the storage medium is not limited to a medium independent from a computer or a built-in system; a storage medium storing or temporarily storing a program downloaded through local area network (LAN) or the Internet, etc. is also adoptable. Furthermore, the functions of the processing circuitry 131 may be executed not only by means of one storage medium, but also of multiple storage media. In this case, any storage format is adaptable as well.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A magnetic resonance imaging apparatus comprising processing circuitry configured to:
    calculate inverse characteristics of a $B_1$ sensitivity map in an imaging area of a subject;
    fit a multi-degree polynomial function to the inverse characteristics of the $B_1$ sensitivity map;
    calculate positions in k-space, amplitudes and phases of a plurality of RF pulses by associating the polynomial function fit to the inverse characteristics with a relational expression between the RF pulses and k-space; and
    control application of the RF pulses in accordance with the positions, the amplitudes and the phases,
    wherein the polynomial function and the relational expression have equal degrees.

2. The apparatus according to claim 1, wherein the relational expression represents a plurality of spokes dispersed in the k-space to design the RF pulses, and the processing circuitry applies the RF pulses in an order along a trajectory of the plurality of spokes.

3. The apparatus according to claim 1, wherein the processing circuitry selects a polynomial function to perform fitting, in accordance with an imaging target of the subject.

4. The apparatus according to claim 1, wherein the processing circuitry calculates the positions and the phases based on characteristics of a quadric curve and a discriminant.

5. The apparatus according to claim 2, wherein one of the plurality of spokes is placed at an origin of the k-space, and
    the processing circuitry sets a conditional equation so that an amplitude of an RF pulse corresponding to the spoke at the origin does not become a negative value.

6. The apparatus according to claim 1, wherein the processing circuitry changes an approximation method of the relational expression if a phase in the relational expression is deviated from zero degrees by a threshold value or more.

7. The apparatus according to claim 3, wherein the processing circuitry deviates a phase in the relational expression by $\pi$, if a $B_1$ strength distribution for the imaging target is symmetric, and the polynomial function opens upward.

8. The apparatus according to claim 1, wherein the processing circuitry multiplies a desired flip angle by a value obtained by dividing an amplitude of a first RF pulse by a sum of amplitudes of the RF pulses, and calculates a flip angle by the first RF pulses.

9. The apparatus according to claim 1, further comprising a storage configured to store a table indicating correspondence information between an imaging condition including information relative to the subject and the relational expression,
    wherein the processing circuitry refers to the table and determines the relational expression in accordance with the subject.

10. A pulse design method comprising:
    calculating inverse characteristics of a $B_1$ sensitivity map in an imaging area of a subject;
    fitting a multi-degree polynomial function to the inverse characteristics of the $B_1$ sensitivity map;
    calculating positions in k-space, amplitudes and phases of RF pulses by associating the polynomial function fit to the inverse characteristics with a relational expression between RF pulses and k-space; and
    controlling application of the RF pulses in accordance with the positions, the amplitudes and the phases,
    wherein the polynomial function and the relational expression have equal degrees.

* * * * *